United States Patent [19]

Lentz et al.

[11] Patent Number: 5,607,478
[45] Date of Patent: Mar. 4, 1997

[54] YARN WRAPPED PTFE TUBULAR PROSTHESIS

[75] Inventors: David J. Lentz, Randolph; Nick Popadiuk, Hillsborough, both of N.J.; Peter Schmitt, Garnerville, N.Y.; Edward J. Dormier, Rockaway; Richard J. Zdrahala, Montville, both of N.J.

[73] Assignee: Meadox Medicals Inc., Oakland, N.J.

[21] Appl. No.: 616,047

[22] Filed: Mar. 14, 1996

[51] Int. Cl.⁶ .................. A61F 2/04; A61F 2/06
[52] U.S. Cl. ........................ 623/12; 623/1
[58] Field of Search ................. 623/1, 12, 11; 600/36; 606/157

[56] References Cited

U.S. PATENT DOCUMENTS

| | | |
|---|---|---|
| 3,105,492 | 11/1963 | Jeckel . |
| 3,479,670 | 11/1969 | Medell . |
| 4,082,893 | 4/1978 | Okita . |
| 4,208,745 | 6/1980 | Okita . |
| 4,248,924 | 2/1981 | Okita . |
| 4,283,448 | 8/1981 | Bowman . |
| 4,332,035 | 6/1982 | Mano . |
| 4,385,093 | 5/1983 | Hubis . |
| 4,478,665 | 10/1984 | Hubis . |
| 4,478,898 | 10/1984 | Kato . |
| 4,550,447 | 11/1985 | Seiler, Jr. et al. . |
| 4,647,416 | 3/1987 | Seiler, Jr. et al. . |
| 4,713,070 | 12/1987 | Mano . |
| 4,816,339 | 3/1989 | Tu et al. . |
| 4,822,361 | 4/1989 | Okita et al. . |
| 4,955,899 | 9/1990 | Della Corna et al. . |
| 4,973,609 | 11/1990 | Browne . |
| 5,061,276 | 10/1991 | Tu et al. . |

FOREIGN PATENT DOCUMENTS

| | | |
|---|---|---|
| 232543A2 | 8/1987 | European Pat. Off. . |
| 256748A2 | 2/1988 | European Pat. Off. . |
| 6189984 | 7/1994 | Japan ........................... 623/1 |
| 892980 | 4/1962 | United Kingdom . |

*Primary Examiner*—Debra S. Brittingham
*Assistant Examiner*—Tram Anh T. Nguyen
*Attorney, Agent, or Firm*—Hoffmann & Baron

[57] ABSTRACT

An implantable microporous ePTFE tubular vascular graft exhibits long-term patency, superior radial tensile strength, reduction in tear propagation, and increases in suture retention strength and crush resistance. The graft includes an ePTFE tubular structure having a preselected microporous structure. The tubular structure is wrapped externally with a PTFE yarn in a helical fashion. The helical wrap of yarn is bonded to the exterior surface of the tubular structure by application of heat or heat in combination with force to form a composite structure which substantially maintains the porosity of the underlying tubular structure while increasing the suture retention strength, radial tensile strength, crush resistance, and tear propagation resistance.

12 Claims, 4 Drawing Sheets

YARN WRAPPED PTFE TUBULAR PROSTHESIS

FIELD OF THE INVENTION

The present invention relates generally to PTFE tubular prosthesis. More particularly, the present invention relates to a tubular graft formed of ePTFE which exhibits enhanced radial tensile strength, improved suture retention strength, and a reduction in tear propagation by providing a helical wrapping of PTFE yarn therearound.

BACKGROUND OF THE INVENTION

The use of polytetrafluoroethylene (PTFE) to form tubular vascular prostheses is well known. PTFE is particularly suitable as an implantable prosthesis as it exhibits superior biocompatability. PTFE tubes may be used as vascular grafts in the replacement and repair of blood vessels, as PTFE exhibits low thrombogenicity. In vascular applications, grafts are manufactured from expanded polytetrafluoroethylene (ePTFE), as tubes formed therefrom have a microporous structure which allows natural tissue ingrowth and cell endothelialization once implanted in the vascular system. Such structure contributes to the long term healing and patency of the graft.

Vascular ePTFE grafts are made by a paste extrusion process wherein PTFE including a lubricant is extruded into a tubular shape. This tubular extruded product, known as a green tube, is then expanded, typically in the axial direction, to form an ePTFE tube. Grafts formed of ePTFE have a fibrous state defined by interspaced nodes interconnected by elongate fibrils. The fibrils have a tendency to align themselves along the axis of expansion; that is, along the longitudinal direction of the tube. The spaces between the nodes and fibrils of the ePTFE tube define a microporous structure which enhances tissue ingrowth and cell endothelialization. While such microporous structure is beneficial to the healing characteristics of the graft, the alignment of the fibrils along the axis of the graft has a tendency to produce a graft with anisotropic physical properties, for example reduced burst and radial tensile strength of the graft. Further, such microporous structure also increases the likelihood of a tear propagating along the length of the graft. This is especially significant during implantation, when the surgeon places a suture hole in the graft, and during secondary surgical procedures such as thrombectomy. The hole or slit placed in the graft during such procedures may serve as a failure initiation zone and have a tendency to propagate a tear longitudinally along the graft. Finally, such a highly organized fibril structure produces reduced longitudinal suture retention strength, increasing the likelihood of suture pull out during implantation.

Attempts have been made to increase the radial and suture retention strengths as well as to reduce the likelihood of tear propagation in ePTFE grafts. As an example, various techniques have been developed to change the node and fibril arrangement defining the microporous structure of the graft such that the fibrils are aligned more in a randomized direction with respect to the longitudinal axis of the graft.

Manufacturing techniques, such as rotating the extrusion die components which form the green tube, have been employed in an effort to orient the fibrils in a non-longitudinal direction. In this manner, upon expansion, the resulting vascular graft exhibits more randomness in fibril orientation. Other techniques to enhance radial tensile strength, improve suture retention strength, and reduce the likelihood of tear propagation, employ multi-layer structures in forming vascular grafts. These multi-layer ePTFE structures may include sheets, tubes, or tape wraps of various oriented ePTFE structures which, when combined, form a composite structure wherein a more randomized distribution of fibrils exists. However, these multi-layered structures significantly affect the porosity of the composite graft. The porosity of the graft, defined by the microporous structure, is preselected such that it exhibits the desired combination of characteristics leading to sufficient strength and appropriate porous microstructure to facilitate tissue ingrowth and cell endothelialization. By changing the microporous structure using multi-layered structures, the desired porosity characteristics are also changed. Other multi-layered structures may include PTFE tubes over-wrapped with non-PTFE filaments, intended primarily to increase the compression resistance of the resulting composite. Such structures do not address the aforementioned strength issues of the ePTFE graft, and the use of dissimilar material may adversely impact the long-term structural integrity of the composite, thus affecting its biocompatibility.

It is therefore desirable to provide an ePTFE vascular graft which exhibits a high degree of radial tensile strength, as well as reduced tear propagation tendency while still maintaining a desired porosity. It is further desirable to provide an ePTFE graft which exhibits superior suture retention strength.

SUMMARY OF THE INVENTION

It is an object of the present invention to provide an improved ePTFE vascular graft.

It is a further object of the present invention to provide an ePTFE vascular graft exhibiting desired porosity while establishing enhanced radial tensile strength, tear resistance, and suture retention strength.

It is still a further object of the present invention to provide a vascular graft, formed of an ePTFE tube having wrapped therearound a yarn of PTFE which increases the radial tensile strength of the graft, as well as reduces the tendency of the graft to propagate a tear longitudinally therealong, while substantially maintaining the desired porosity characteristics of the ePTFE tube.

It is yet another object of the present invention to provide an ePTFE vascular graft having improved compression or crush resistance.

In the efficient attainment of these and other objectives, the present invention provides an implantable tubular prosthesis. The tubular prosthesis is formed by an expanded polytetrafluoroethylene (ePTFE) tube having a microporous structure defined by nodes interconnected by fibrils. At least one winding of a multifilament polytetrafluoroethylene (PTFE) yarn is helically wrapped externally about the tube along the length thereof to form a composite structure. The resultant composite structure substantially exhibits a porosity defined by the underlying ePTFE tube while exhibiting a high degree of radial tensile and longitudinal suture retention strengths as well as a reduction in the tendency of a suture or surgical incision to propagate a tear therealong.

As more particularly described by way of the preferred embodiments herein, the multifilament PTFE yarn may be flattened such that the plural filaments of the yarn are in increased contact with the exterior surface of the ePTFE tube. The yarn may then be bonded to the tube by application of heat or pressure and heat to form a composite structure. It is further contemplated that various strength property levels may be established by controlling the amount of helical windings of multifilament PTFE yarn about the exterior of the ePTFE tube. Additionally, multifilament yarns may be wrapped in opposing directions to form a crossing pattern there over, thereby further enhancing the beneficial attributes attained. Finally, it is contemplated that the manner in which the PTFE yarn is bonded to the ePTFE tube may be varied to establish various combinations of desirable strength, handling characteristics, and porosity.

DETAILED DESCRIPTION OF THE PREFERRED EMBODIMENTS

The composite prosthesis of the preferred embodiments of the present invention is a multi-component tubular structure which is particularly suited for used as an endoprosthesis, specifically a vascular graft. The prosthesis is formed of extruded polytetrafluoroethylene (PTFE) as PTFE exhibits superior biocompatability. Further, PTFE is particularly suitable for vascular applications as it exhibits low thrombogenicity. Tubes formed of extruded PTFE may be expanded to form ePTFE tubes where the ePTFE tubes have a desired fibrous state which is defined by elongated fibrils interconnecting spaced apart nodes. Such node/fibril arrangement defines a microporous structure, the porosity of which is determined by the distances between the nodes generally referred to as the internodal distance (IND). In forming tubular vascular grafts, the porosity of the tubular structure is selected so as to have desirable healing characteristics. A balance must be achieved between a porosity sufficient to permit endothelialization and tissue ingrowth, while concurrently providing a structure which exhibits sufficient physical integrity, such as that measured by radial tensile and suture retention strengths, to successfully function as a vascular graft. The present invention provides a tubular structure which exhibits enhanced radial tensile strength, increased tear resistance, and superior longitudinal suture retention strength without significantly reducing the porosity necessary to establish long term patency of the graft.

Figure 1:
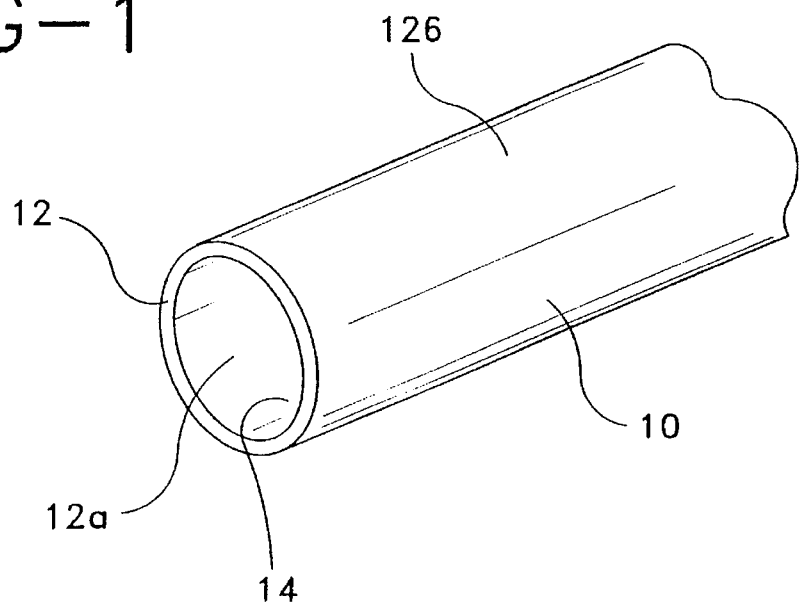
FIG. 1 is a perspective showing a portion of an ePTFE tube used in accordance with the present invention.
Figure 2:
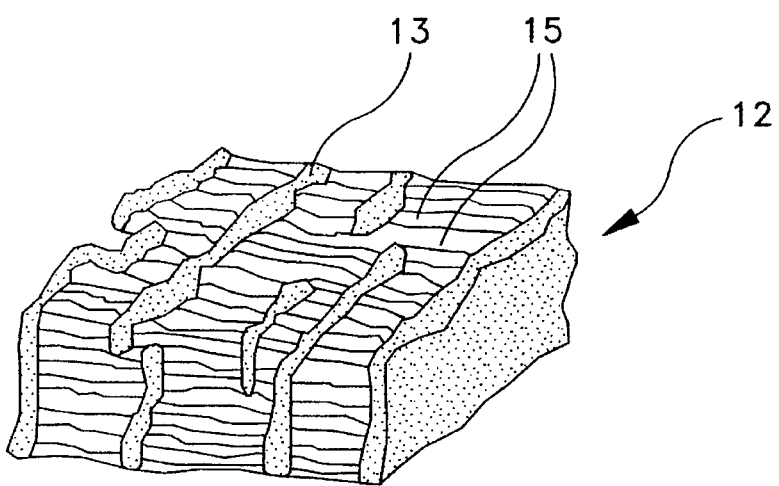
FIG. 2 is a schematic representation of the microstructure of the wall of the ePTFE tube of FIG. 1.

Referring to FIGS. 1 and 2 of the drawings, a tubular ePTFE structure useful as a vascular graft tube 10 is shown. Graft tube 10 includes a generally cylindrical wall 12 having inner and outer surfaces 12a and 12b, respectively. Graft tube 10 defines an inner lumen 14 extending longitudinally therethrough. The inner lumen permits the passage of blood through graft tube 10 once it is properly implanted in the vascular system. Graft tube 10 is formed of PTFE in a paste extrusion process. The process for the paste extrusion of PTFE tubes is well known in the extrusion art. A billet of PTFE and lubricant is extruded in an axial direction to form a tubular green tube. Once extruded, the green tube is expanded to form ePTFE graft tube 10. The ePTFE graft tube 10 includes nodes 13 and fibrils 15 in an arrangement which defines the microporous structure thereof.

Generally, tubes may be expanded using preselected processing parameters such as rates of expansions and temperature at various processing stages which develop a desired microporous structure. The specifically selected microporous structure of the resulting graft tube has predetermined porosity suitable to enhance the long term patency of the graft by allowing enhanced tissue ingrowth and cell endothelialization, thus providing good healing characteristics.

In a specific embodiment of the present invention, the tubular structure 10 may be formed by expanding a PTFE tube at a relatively high degree of elongation on the order of approximately between .200% and 1000% elongation, preferably from about between 300% and 400%. The green tube is expanded at a temperature between room temperature and 645° F., preferably between about 400° F. and 500° F. The tube is then preferably, but not necessarily, fully sintered after expansion. Sintering is typically accomplished by heating the expanded tube at a temperature between 620° F. and 800° F., preferably about 660° F. and for a time between 30 seconds and 30 minutes, preferably about 15 minutes. The resulting expanded graft tube 10 is suitable for use as an implantable vascular graft.

Figure 3:
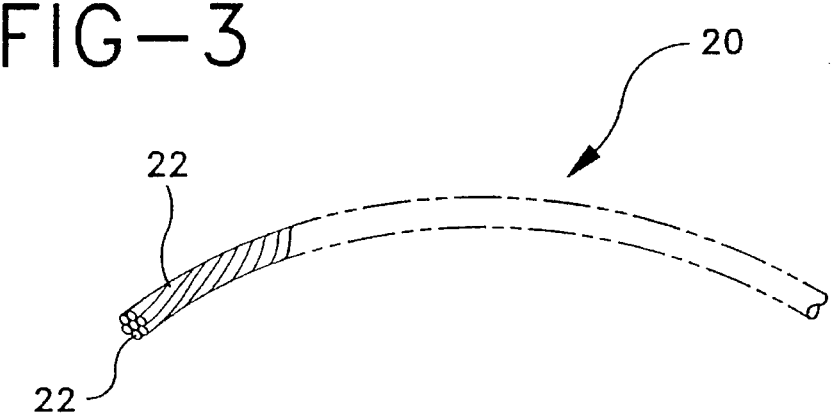
FIG. 3 is a perspective showing of a portion of a PTFE yarn used in accordance with the present invention.

In order to achieve enhanced properties, especially properties relating to radial tensile strength, reduced suture hole tear propagation, increased suture retention strengths, and increased compression resistance, the graft tube 10 is wrapped with a PTFE yarn 20 shown in FIG. 3.

Yarn 20 is a nonporous PTFE multifilament yarn which is of common commercial variety. In the present invention, yarn 20 includes approximately between 10 and 200 individual filaments and has a denier between approximately 200 and 1500. The filaments of such PTFE yarns are highly oriented during their manufacture, resulting in a desirable stress-strain deformation behavior, and a resistance to both stress induced flow of the fiber at non-elevated temperatures and relaxation induced shrinkage up to moderate temperatures. Such yarns typically possess tenacity between approximately 0.8 and 3.0 g/denier.

Preferably, but not necessarily, the yarn 20 may be flattened to as to spread apart the individual filaments 22 in a planar orientation. The flattening of the multifilament yarn 20 is defined as splaying. Such splaying may be accomplished prior to wrapping yarn 20 around graft tube 10, or after the wrapping of graft tube 10 with yarn 20. The splaying of the multifilament yarn 20 increases the surface contact area between the yarn and the outer surface 12b of graft tube 10 allowing more complete bonding of the yarn filaments to the graft tube. Such splaying also results in a lower yarn profile above the surface of graft tube 10.

Figure 4:
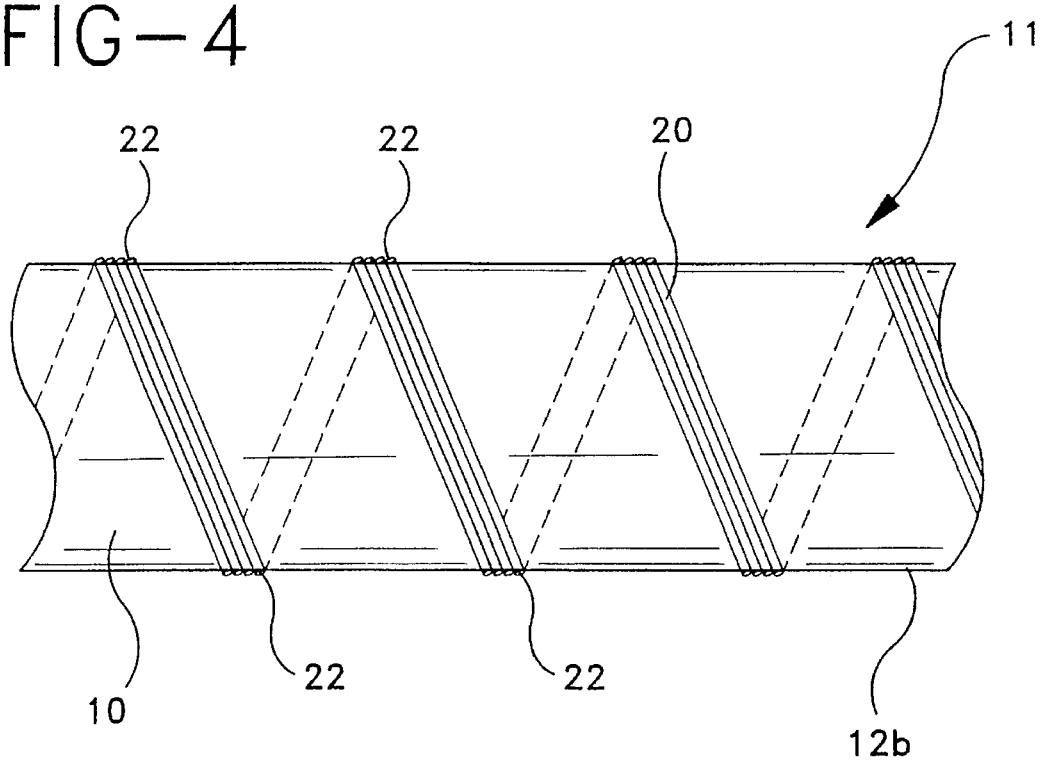
FIGS. 4 and 5 show successive steps which may be employed in forming a yarn-wrapped ePTFE vascular graft in accordance with the present invention.
Figure 5:
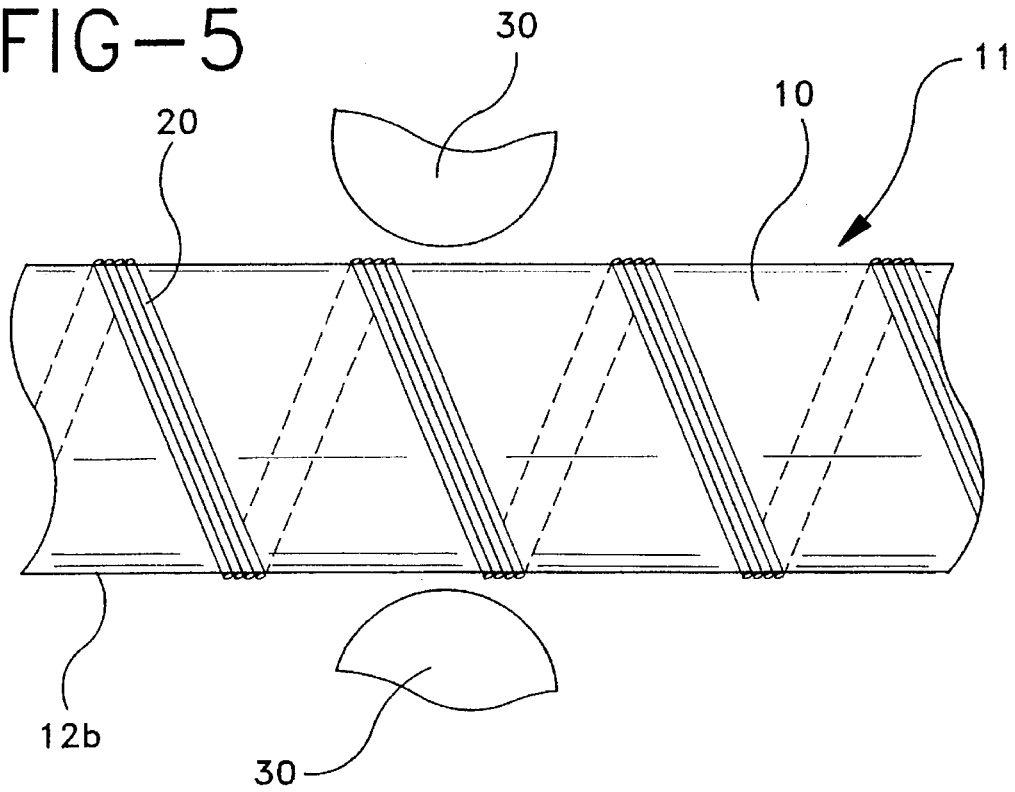

Referring to FIGS. 4 and 5, the wrapping of yarn 20 about tube 10 may be described. Tube 10 is placed over a stainless steel or other suitable mandrel. The mandrel containing tube 10 is then rotated as yarn 20 is wrapped about the external surface 12b of tube 10 in a helical orientation to form a composite graft tube 11. The density of the wrap, i.e., the spacing of successive helical windings, may be varied so as to vary the coverage of the yarn over the external surface 12b. The wrappings may be varied from helical windings which are significantly spaced apart, thereby decreasing the density of coverage, to tightly spaced windings where the external surface 12b of tube 10 is nearly fully covered. In varying the density of the helical windings the balance between healing characteristics and physical strength is so varied.

In a preferred embodiment where the tubular structure has an internal diameter (ID) of about between 3 and 10 mm and a wall thickness of about between 0.3 mm and 1.2 mm, the density of coverage is approximately 20 wraps per inch of tube length. The wrapping is done in a single direction as shown in FIG. 4. As described hereinabove, the yarn 20 is splayed after wrapping, but before the yarn is fixed to tube 10. However, it is contemplated that yarn 20 may be splayed prior to wrapping, and then wrapped around tube 10.

Adhesion of the yarn 20 to the outer surface 12b of tube 10 may be achieved through the use of heat. The graft tube 10 wrapped with yarn 20 as described above, and still maintained on the stainless steel mandrel, is placed in an oven at a temperature between approximately 620° F. and 800° F. for a time ranging from approximately 20 seconds to 15 minutes. Most preferably, the assembly is heated at 660° F. for a period of 10 minutes. The graft is removed from the oven, cooled to ambient temperature, and removed from the mandrel.

In a preferred embodiment, heat may be used in combination with force to achieve a bond between yarn 20 and the outside surface 12b of tube 10. As indicated in FIG. 5, the composite graft tube, maintained on the mandrel used for wrapping, is passed through a pair of opposed spaced apart heated rollers 30. Rollers 30 apply a preselected force from approximately 0 N/(M of contact length) to 250 N/(M of contact length). In addition, the rollers 30 are heated to a temperature of approximately between 620° F. to 750° F. so as to achieve a suitable bond between the yarn 20 and the tubular structure 10. In a preferred embodiment, the surface velocity of the rollers 30 is matched to the surface velocity of the graft tube to inhibit relative motion and eliminate torsional forces from being imparted to the graft surface during yarn bonding. It is envisioned that various combinations of contact time, temperature, and relative velocities between the rotating roller surfaces and graft surface may be employed to achieve a predetermined bond strength and resultant composite structure. After the entire length of the graft has been passed through rollers 30, the graft is cooled to ambient temperature and removed from the mandrel.

Figure 7:
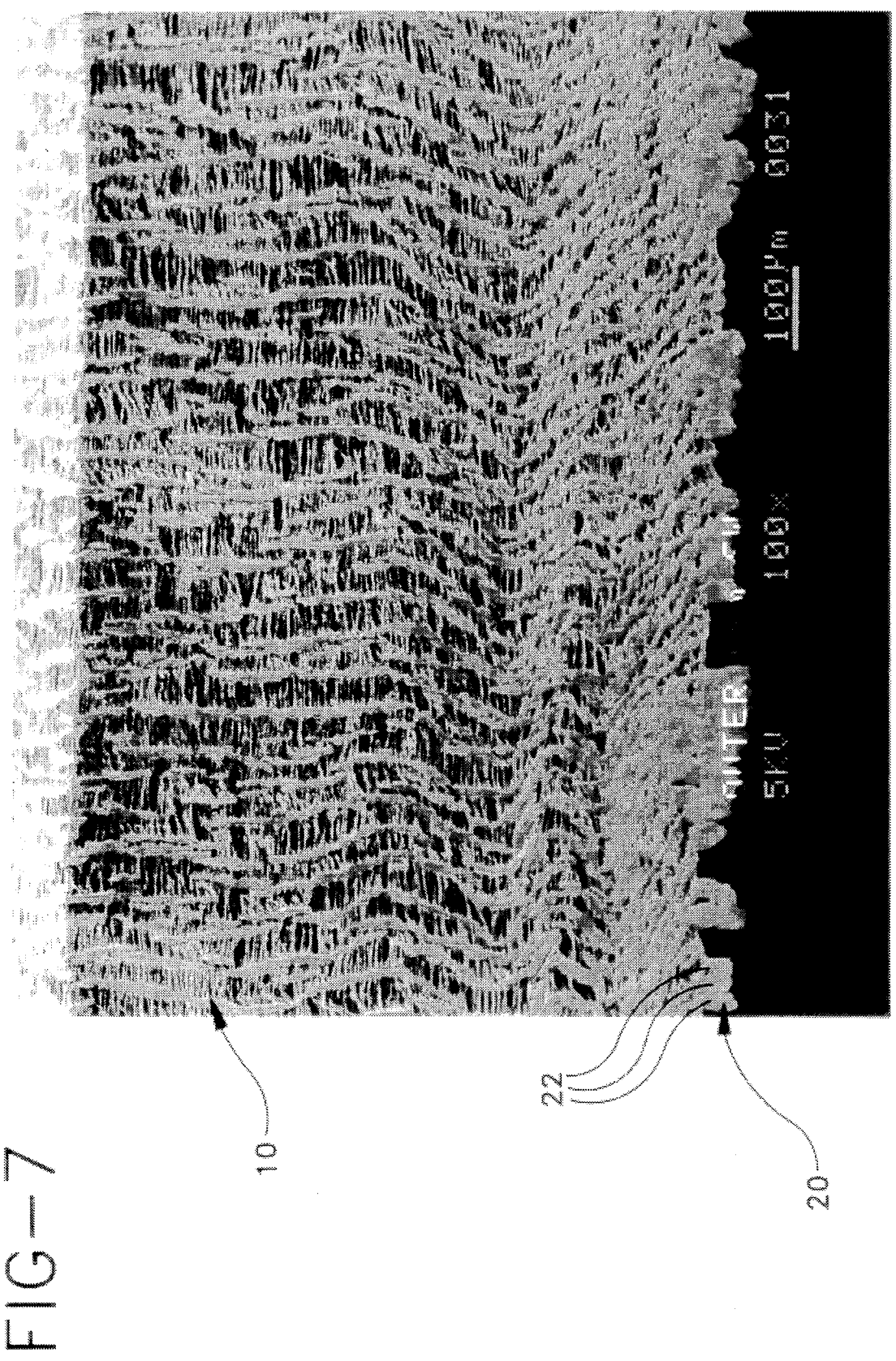
FIG. 7 is a scanning electron micrograph, showing a generally cross-sectional view of a portion of the yarn wrapped ePTFE vascular graft produced in accordance with the present invention.

The resulting composite graft (FIG. 7) exhibits enhanced suture retention strength, increased radial tensile strength and resistance to tear propagation caused by a suture placement or incision related to secondary surgical procedures such as thrombectomy. Additionally, the resulting composite graft exhibits enhanced compression resistance allowing it to withstand higher compressive forces without concern of lowering of blood flow rate. Such benefits are achieved without significantly changing the porosity of the graft, as the base tube 10 maintains its' node/fibril orientation defining the porosity of the graft.

Figure 6:
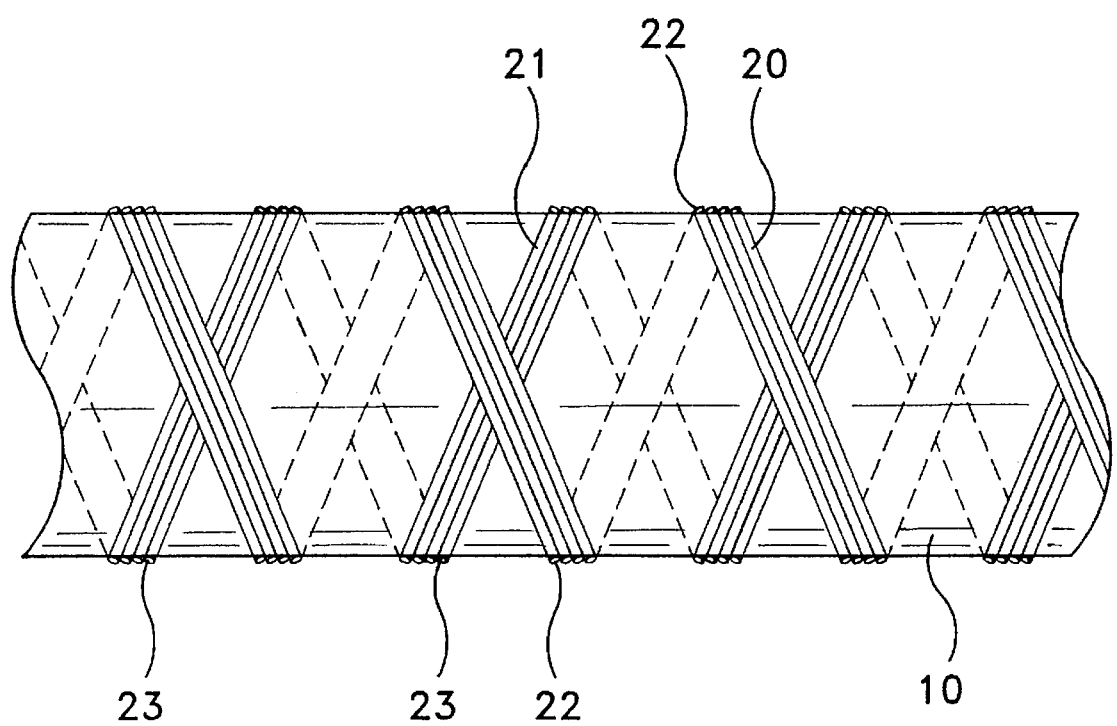
FIG. 6 shows a further embodiment of the yarn wrapped ePTFE of the present invention.

As shown in FIG. 6, a further embodiment of the present invention may be described. Tube 10 may be wrapped with a yarn 20 in a manner described above with respect to FIG. 4. However, before application of heat or heat and force to bond the yarn 20 to the tube 10, an additional yarn 21 may be helically wrapped there over. Yarn 21, which may be substantially similar to yarn 20 or of an alternative denier/number of filaments, may be wrapped in a crossing pattern in a direction opposite to the direction of wrapping of yarn 20. This crossing pattern provides further enhancement in radial tensile strength, suture retention strength and the resistance to suture hole elongation, exceeding that improvement realized by wrapping in a single direction.

The following examples serve to provide further appreciation of the invention, but are not meant in any way to restrict the scope of the invention:

EXAMPLE 1

6 mm ID PTFE extruded green tubes were prepared in accordance with standard PTFE paste extrusion procedures. The resultant green tubes were expanded to 375% elongation and fully sintered to produce ePTFE tubes having an inner diameter of 6.02 mm and a wall thickness of 0.72 mm. A set of these tubes were yarn wrapped in accordance with the method of the present invention at a yarn coverage of 22 wraps/inch to produce single helically wrapped samples as shown schematically in FIG. 4. Several of these tubes were then wrapped in the opposing direction according to the art of the present invention to produce double helically wrapped samples as shown schematically in FIG. 6. The resultant composite tubes were heated in an oven at 660° F. for 12 minutes, cooled to ambient temperature, and removed from their mandrels. The tubes of Example were tested in accordance with standard AAMI and ASTM test protocols and yielded the results contained in Table I.

TABLE I

| | WRAP CONFIGURATION | | |
|---|---|---|---|
| | Unwrapped Tube | 22 Wraps/Inch Non Splayed Single Helical | 22 Wraps/Inch Non Splayed Double Helical |
| Tear Resistance (g) | 239 | 481 | 678 |
| Suture Retention Strength (g) | 430 | 447 | 533 |
| Radial Tensile Strength (Kg/mm$^2$) | 0.43 | 0.60 | 0.77 |
| Crush Resistance (g/mm2) | 10.8 | 12.4 | 12.6 |
| Yarn Retention Strength (g) | NO WRAP | 6.5 | 8.4 |

The composite yarn-wrapped structures result in substantially increased key physical property characteristics above that of the unwrapped ePTFE substrate tube. Additionally, utilization of the double helical yarn wrap configuration shown schematically in FIG. 6, further increases the physical properties. Most notably, the addition of a single helical wrap increases the tear resistance by 101%, radial tensile strength by 40% and crush resistance by 15%. The use of the double helical wrap configuration results in a 185% increase in tear resistance, 80% increase in suture retention strength, 80% increase in radial tensile strength and an increase in crush resistance of 17%.

EXAMPLE 2

6 mm ID PTFE extruded green tubes were prepared in accordance with standard PTFE paste extrusion procedures. The resultant green tubes were expanded to 375% elongation and fully sintered to produce ePTFE tubes having an inner diameter of 6.02 mm and a wall thickness of 0.72 mm. A set of these tubes were yarn wrapped in accordance with the method of the present invention at a yarn coverage of 22 wraps/inch to produce double helically wrapped samples as shown schematically in FIG. 6. The resultant composite tubes were handled in such a manner to splay the yarn, resulting in an increased surface contact between the yarn filaments and the tube surface. A portion of these composite tubes were heated in an oven at 660° F. for 12 minutes. The remaining tubes were heated under force as shown schematically in FIG. 5 using a heated roller surface temperature of 685° F. The tubes of Example 2 were tested in accordance with standard AAMI and ASTM test protocols and yielded the results contained in Table II.

TABLE II

YARN ADHESION METHOD (SPLAYED YARN)

| | 22 Wraps/Inch Double Helical Oven Heated | 22 Wraps/Inch Double Helical Heated Rollers |
|---|---|---|
| Tear Resistance (g) | 601 | 620 |
| Suture Retention Strength (g) | 421 | 582 |
| Radial Tensile Strength (Kg/mm$^2$) | 0.70 | 0.70 |
| Crush Resistance (g/mm2) | 11.0 | 13.2 |
| Yarn Retention Strength (g) | 9.7 | 14.1 |

Most notably, the use of force in combination with heat (heated rollers) to achieve bonding between the PTFE yarn wrap and the substrate ePTFE tube results in a substantial increase in yarn retention strength and a significant improvement in suture retention strength over similar tubes employing heat without force (oven heated). Additionally, the overall consistency of the yarn adhesion is improved through the use of both force and heat during bonding of the PTFE yarn.

EXAMPLE 3

4 mm, 6 mm, and 10 mm ID PTFE extruded green tubes were prepared in accordance with standard PTFE paste extrusion procedures. The resultant 6 and 10 mm green tubes were expanded to 375% elongation and fully sintered to produce ePTFE tubes having an inner diameter of 5.9 mm and a wall thickness of 0.40 mm and an inner diameter of 9.80 mm and a wall thickness of 0.69 mm respectively. The resultant 4 mm green tubes were expanded to 300% elongation and fully sintered to produce ePTFE tubes having an inner diameter of 4.08 mm and a wall thickness of 0.60 mm. A set of each tube size tubes were yarn wrapped in accordance with the method of the present invention at a yarn coverage of 22 wraps/inch to produce double helically wrapped samples as shown schematically in FIG. 6. The resultant composite tubes were handled in such a manner to splay the yarn, resulting in an increased surface contact between the yarn filaments and the tube surface. The tubes were heated under force as shown schematically in FIG. 5 using a heated roller surface temperature of 685° F. The tubes of Example 3 were tested in accordance with standard AAMI and ASTM test protocols and yielded the results contained in Tables III–V.

TABLE III

TUBE SIZE - 5.9 mm ID/0.40 mm Wall

| | Unwrapped Tube | 22 Wraps/Inch Double Helical Heated Rollers |
|---|---|---|
| Tear Resistance (g) | 122 | 456 |
| Suture Retention Strength (g) | 136 | 391 |
| Radial Tensile Strength (Kg/mm$^2$) | 0.5 | 0.8 |
| Crush Resistance (g/mm2) | 2.3 | 5.6 |

TABLE IV

TUBE SIZE - 9.8 mm ID/0.69 mm Wall

| | Unwrapped Tube | 22 Wraps/Inch Double Helical Heated Rollers |
|---|---|---|
| Tear Resistance (g) | 280 | 830 |
| Suture Retention Strength (g) | 341 | 617 |
| Radial Tensile Strength (Kg/mm$^2$) | 0.6 | 0.6 |
| Crush Resistance (g/mm2) | 1.8 | 5.2 |

TABLE V

TUBE SIZE - 4.1 mm ID/0.60 mm Wall

| | Unwrapped Tube | 22 Wraps/Inch Double Helical Heated Rollers |
|---|---|---|
| Tear Resistance (g) | 301 | 638 |
| Suture Retention Strength (g) | 331 | 657 |
| Radial Tensile Strength (Kg/mm$^2$) | 0.6 | 1.04 |
| Crush Resistance (g/mm2) | 18.1 | 18.2 |

As indicated by the data of Tables III, IV, and V the advantages imparted by the method of the current invention are shown to be generally applicable to ePTFE tubes of broadly varying wall thickness and diameters of interest in vascular repair.

Various changes to the foregoing described and shown structures would now be evident to those skilled in the art. Accordingly, the particularly disclosed scope if the invention is set forth in the following claims.

What is claimed is:

1. An implantable tubular prosthesis comprising an expanded polytetrafluoroethylene (ePTFE) tube having a microporous structure defined by nodes interconnected by fibrils, said tube having a length; and at least one winding of a non-porous, non-elastic multifilament yarn helically wrapped externally about at least a portion of said tube along the length thereof, said yarn consisting essentially of polytetrafluoroethylene (PTFE).

2. An implantable tubular prosthesis of claim 1 wherein said multifilament PTFE yarn is flattened so that plural filaments of said yarn are in contact with said tube.

3. An implantable tubular prosthesis of claim 1 wherein said yarn is bonded to said tube.

4. An implantable tubular prosthesis of claim 3 wherein said yarn is bonded to said tube with heat.

5. An implantable tubular prosthesis of claim 3 wherein said yarn is bonded to said tube with heat and force.

6. An implantable tubular prosthesis of claim 1 wherein said at least one winding of said multifilament yarn are helically wrapped about said tube.

7. An implantable tubular prosthesis of claim 6 wherein said winding comprising at least two windings are wrapped about said tube in opposite helical directions and wherein the winding of one said yarn overlaps the winding of the other said yarn.

8. An implantable tubular prosthesis of claim 1 wherein each of said windings of said yarn are spaced apart a uniform distance.

9. An implantable tubular prosthesis of claim 8 wherein said uniform distance is between about 0.5 mm and 5 mm.

10. An implantable tubular prosthesis of claim 8 wherein said uniform distance is about 1.2 mm.

11. An implantable tubular prosthesis of claim 1 wherein said multifilament yarn is between 200 and 1500 denier.

12. An implantable tubular prosthesis of claim 1 wherein said multifilament yarn is 225 denier.

* * * * *